United States Patent
Ramaswamy et al.

(10) Patent No.: US 6,235,485 B1
(45) Date of Patent: *May 22, 2001

(54) HELIOTHIS VIRESCENS-SPECIFIC AND HELICOVERPA ZEA-SPECIFIC MONOCLONAL ANTIBODIES AND INSECT IDENTIFICATION METHOD

(75) Inventors: Sonny B. Ramaswamy; Fanrong Zeng, both of Manhattan, KS (US); Stephen B. Pruett, Shreveport, LA (US)

(73) Assignee: Mississippi State University, Mississippi State, MS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,415

(22) Filed: Feb. 18, 1998

(51) Int. Cl.$^7$ .................. G01N 33/53; G01N 33/543; A61K 39/395; A61K 38/00; C12N 9/02
(52) U.S. Cl. .................. 435/7.1; 435/7.92; 435/189; 435/348; 424/130.1; 424/432.1; 424/141.1; 424/151.1; 514/12; 436/518
(58) Field of Search .................. 424/130.1, 132.1, 424/141.1, 151.1; 435/7.1, 7.92, 189, 348; 514/12

(56) References Cited

U.S. PATENT DOCUMENTS

| 5,656,437 | 8/1997 | Greenstone | 435/7.1 |
| 5,871,939 | * 2/1999 | Trowell et al. | 435/721 |

FOREIGN PATENT DOCUMENTS

| 2114160 | 1/1994 | (CA) . |
| 672453 | 1/1994 | (AU) . |

OTHER PUBLICATIONS

Pest Control & Sustainable Agriculture, pp. 176–179, 1993, S.C. Trowell, et al., "A Heliothis Identification Kit".

Annals of the Entomological Society of America, vol. 82, pp. 45–49, 1989 Greenstone, et al., "Predation on *Heliothis Zea*(Lepidoptera: Noctuidae): An Instar–Specific ELISA Assay for Stomach Analysis".

Journal of Economic Entomology, vol. 88, No. 2, pp. 213–218, Greenstone, "Bollworm or Budworm? Squashblot Immunoassay Distinguishes Eggs of *Helcoverpa Zea* and *Heliothis Virescens* (Lepidoptera: Noctuidae)".

Annals of the Entomological Society of America, vol. 83, No. 6, pp. 1101–1107, Stuart, et al., 1990 "Beyond ELISA: A Rapid, Sensitive, Specific Immunodot Assay for Indentification of Predator Stomach Contents".

Annals of the Entomological Society of America, vol. 90, No. 1, pp. 83–90, 1996, Goodman, et al., "Monoclonal Antibodies to Vitellins of Bollworm and Tobacco Budworm (Lepidoptera: Noctuidae): Biochemcial and Ecological Implications".

Entomol. Exp. Appl. 68:1–7, 1993, Greenstone, et al., "Determinatin of Prey Antigen Half–Life in Polistes Metricus Using a Monoclonal Antibody–Based Immunodot Assay".

Enviromental Entomology, vol. 18, No. 2, pp. 195–200, (1988), Greenstone, "Foreign Exploration for Predators: A Proposed New Methodology".

Lenz et al. Arch. Insect. Biochem. Physiol 9:167–178, 1988.*

* cited by examiner

*Primary Examiner*—Rodney P. Swart
*Assistant Examiner*—Padma Baskar
(74) *Attorney, Agent, or Firm*—Piper, Marbury Rudnick & Wolfe, LLP; Steven B. Kelber

(57) ABSTRACT

Immunoassays useful for distinguishing between the insect pests *Heliothis virescens* and *Helicoverpa zea* are disclosed. These immunoassays employ either *Heliothis virescens*-specific monoclonal antibodies which do not detectably cross-react with tissue of *Helicoverpa zea*, or *Helicoverpa zea*-specific antibodies which do not detectably cross-reict with tissue of *Heliothis virescens*. Thus, use of these antibodies in immunoassays conclusively demonstrates the presence of either *Heliothis virescens* or *Helicoverpa zea* organisms on crop plants tested. Also disclosed are *Heliothis virescens*-specific monoclonal antibody which does not detectably cross-react with tissue of *Helicoverpa zea*, and *Helicoverpa zea*-specific monoclonal antibody which does not detectably cross-react with tissue of *Heliothis virescens*. These antibodies can be used in the disclosed immunoassays, and can be included in kits for conducting the disclosed immunoassays.

20 Claims, No Drawings

HELIOTHIS VIRESCENS-SPECIFIC AND HELICOVERPA ZEA-SPECIFIC MONOCLONAL ANTIBODIES AND INSECT IDENTIFICATION METHOD

BACKGROUND OF THE INVENTION

1. Field of the Invention

The present invention relates to immunoassays useful for distinguishing between the insect pests *Heliothis virescens* and *Helicoverpa zea*. More particularly, these immunoassays employ either *Heliothis virescens*-specific antibodies which do not detectably cross-react with eggs of *Helicoverpa zea*, or *Helicoverpa zea*-specific monoclonal antibodies which do not detectably cross-react with eggs of *Heliothis virescens*.

2. Description of the Related Art

*Heliothis virescens* (also known as the tobacco budworm) and *Helicoverpa zea* (also known as the cotton bollworm or corn earworm) both have the capacity to inflict devastating yield losses to agronomically important crops. These two insect pests are typically controlled through the use of pyrethroid and *Bacillus thuringiensis* (Bt) insecticides. However, *Heliothis virescens* has the tendency to become resistant to pyrethroids, while such resistance has not been observed in *Helicoverpa zea*. Conversely, *Helicoverpa Zea* exhibits tolerance to Bt, which does not occur in *Heliothis virescens*.

In order to retard the development of pyrethroid resistance in *Heliothis virescens*, current control methods are aimed at preventing the overexposure of populations of *Heliothis virescens* to pyrethroids. Such control methods would be facilitated if *Heliolthis virescens* and *Helicoverpa zea* populations could be conclusively distinguished in the field at an early stage, e.g., the egg stage. Immunoassays have been used in the past to distinguish between *Heliothis virescens* and *Helicoverpa zea* populations. However, in these immunoassays, antibodies were employed which exhibited at least some degree of cross-reactivity, i.e., the *Helicoverpa zea*-specific antibodies employed cross-reacted with *Heliothis virescens* eggs. Thus, these prior art methods, which are summarized below, were unable to conclusively distinguish between *Heliothis virescens* and *Heiicoverpa zea* organisms.

Trowell et al 1993 (In *Pest Control and Sustainable Agriculture*, ed. S. Corey, D. Dall, W. Milne, pp. 176–179, Melbourne: CSIRO Press) discloses two monoclonal antibodies, designated 70.5.31.11 and 70.7.88.1, which recognize *Helicoverpa armigera* for use in assays to distinguish between *Helicoverpa armigera* and *Helicoverpa punctigerca*. Trowell et al 1993 states that "[w]e believe it will be possible to modify the test kit to allow discrimination of two economically important North American heliothine species, *Heliothis virescens* and *Helicoverpa (Heliothis) zea* . . . "(p. 178, $2^{nd}$ col., $2^{nd}$ full paragraph). However, no evidence is given that these monoclonal antibodies react specifically (i.e., with no detectable cross-reactivity) with either *Heliothis virescens* or *Helicoverpa zea*, or that they react with either of these species at all.

Trowell et al 1994 (Canadian Patent Application 2,114,160) discloses monoclonal antibodies 70.5.31.11 and 70.7.88.1 described above, as well as monoclonal antibody 21.91.2. Trowell et al 1994 states that the antibodies of their invention are "capable of binding a target molecule of *H. zea* but not *Heliothis virescens*." (page 7, lines 32–33). Trowel et al 1994 also states that "[t]he antibody [21.91.2] recognised. *H. zea* but not *Heliothis virescens* . . . " (page 25, lines 6–8).

However, as in Trowell et al 1993, no evidence is given that monoclonal antibodies 70.5.31.11 and 70.7.88.1 react specifically with either *Heliothis virescens* or *Helicoverpa zea*, or that they react with either of these species at all. Moreover, Trowell et al 1994 states that "[a] second batch of supernatant from 21.91.2 was tested and, in this experiment, the inmnunoreactivity appears to be dependent on the concentration of egg proteins (FIG. 1*b*). The best discrimination was observed with dilutions of *H. armigera* and *Heliothis virescens* egg proteins of $\frac{1}{32}$ or $\frac{1}{64}$." (page 25, lines 11–15). Thus, it appears that monoclonal antibody 21.91.2 does cross-react with eggs of *Heliothis virescens*.

Greenstone et al 1989 (Ann. Entomol. Soc. Am. 82:45–49); Stuart et al 1990 (Arm. Entomol. Soc. Am. 83:1101–1107); and Greenstone 1993 (Entomol. Exp. Appl. 68:1–7) disclose the use of immunological assays (i.e., an immunodot assay and an enzyme4 inked immunosorbent assay (ELISA)) to analyze the contents of the stomachs of arthropod predators in predator-prey studies. These assays employ monoclonal antibody HZ5-1 which is specific for *Heiicoverpa zea* arylphorin. HZ5-1 was prepared using hemolymph of fifth instars of *Heiicoverpa zea*. Greenstone et al 1989 states that HZ5-1 "distinguishes remains of [*Helicoverpa zea*] fifth instars in enzyme-linked immunosorbelt assay (ELISA) of fed predator extracts from the remains of the all other instars and eggs of this and related species [e.g., *Heliothis virescens*]." (abstract). Stuart etal 1990 employs HZ5-1 in an immunodot assay and states that "[a] remarkable aspect of our results is the complete lack of overlap in color development between known positives [e.g., fifth inslar *Heiicoverpa zea*] and negatives [e.g., *Heliothis virescens*]—not even a very faint dot is formed in negative assays." (p. 1104, col. 2). However, Greenstone et al 1993 states that "[o]ngoing research utilizing different membranes and other substrates indicates that background can be entirely eliminated, enhancing the distinction between positive and negative results . . . " (p. 5, col. 2 to p. 6, col.1).

Thus, it appears that HZ5-1 recognizes remains of *Heiicoverpa zea* fifth instar larvae, and does not detectably react with *Heliothis virescens*, only if immunoassay conditions are manipulated to eliminate background. In other words, lack of crossreactivity is not an inherent characteristic of HZ5-1, but rather depends on the immunoassay conditions employed. Moreover, in contrast to the monoclonal antibodies of the present invention, HZ5-1 does not react with egg proteins, and therefore cannot be used to identify insects at the egg stage.

Greenstone et al 1995 (J. Econ. Entomol. 88:213–218) describes monoclonal antibody HZE-1 for use in a squash-blot immunoassay to distinguish *Heiicoverpa zea* eggs, from *Heliothis virescens* eggs. HZE-1 was prepared using *Heiicoverpa zea* whole egg homogenate as immunogen. Although HZE-1 is specific for *Heiicoverpa zea* eggs, is Greenstone et al 1995 states that "*H. virescens* eggs sometimes appeared weakly positive when tested on membranes blocked with phenylhydrazine or peroxidase inhibitor . . . " (p. 214, col. 2, $3^{rd}$ full paragraph).

Goodman etal 1997 (Ann. Entomol. Soc. Am. 90:83–90) discloses and characterizes monoclonal antibodies HZE-1 and HVE-1 for use in ecological studies of predation. HVE-1 was prepared using purified *Heliothis virescens* vitellin as inmuunogen. Both antibodies were shown to recognize vitellin specifically. However, HZE-1 recognizes *Helicoverpa armigera* vitellin and *Helicoverpa punctigera* vitellin in addition to *Heiicoverpa zea* vitellin. Furthermore, HVE-1 recognizes vitellins of a number of Helicoverpa and Heliothis species (including *Heiicoverpa zea*), and therefore is not specific for *Heliothis virescens* vitellin only.

Greenstone et al 1997 (U.S. Pat. No. 5,656,437) discloses monoclonal antibody HZE-1. The inventor states that he has "now discovered a hybridoma cell line which produces and secretes a monoclonal antibody which specifically binds to vitellin in the eggs of the corn earworm, *Heiicoverpa zea*, but does not bind to vitellin in the eggs of the tobacco budworm, *Heliothis virescens*." (col. 2, 11. 43–47). Of course, this statement is contradicted by the statement in Greenstone etal 1995 that "*H. virescens* eggs sometimes appeared weakly positive" in an immunoassay employing HZE-1.

Greenstone et al 1997 (U.S. Pat. No. 5,656,437) used only one antibody specific to *Heiicoverpa zea* eggs. Using a single antibody to identify two morphologically similar species can result in false negatives if the eggs are not those of *Heiicoverpa zea*. In the field, eggs of several insect species visually resemble those of *Heiicoverpa zea* and *Heliothis virescens*, increasing the likelihood of obtaining false negative results with just one antibody.

SUMMARY OF THE INVENTION

The present invention solves the problems noted above by providing methods for conclusively distinguishing between *Heliothis virescens* and *Heiicoverpa zea* organisms. Specifically, the present invention is directed to a method for detecting *Heliothis viresciens* or *Heiicoverpa zea* comprising the steps of (a) providing a sample containing a tissue of *Heliothis virescens* or *Heiicoverpa zea*, (b) contacting the sample with an antibody to form an immunological complex containing the tissue and the antibody, and (c) detecting the immunological complex, thereby detecting the tissue. If the detection method is a method for detecting a tissue of *Heliothis verescens*, then the antibody reacts with the tissue of *Heliothis virescens* and does not detectably react with a tissue of *Heiicoverpa zea*. If the detection method is a method for detecting a tissue of *Heiicoverpa zea*, then the antibody reacts with the tissue of *Heiicoverpa zea* and does not detectably react with a tissue of *Heliothis virescens*. Ideally, the tissue is an egg tissue. The antibody is preferably a monoclonal antibody, and may belong to the immunoglobulin isotype IgG (e.g., IgG1 and IgG2a). Advantageously, if the method is a method for detecting *Heliothis verescens*, then the monoclonal antibody is produced by the hybridoma cell line Hv-6-12D-1F4A or Hv-6-12D-6F-4D. If the method is a method for detecting *Heiicoverpa zea*, then the monoclonal antibody is produced by the hybridoma cell line Hz-4-6G-2E-5B or Hz-4-6G-2E-9B. Preferably, the monoclonal antibody does not detectably react with tissue (e.g., egg tissue) of *Spodoptera exigua, Spodoptera frugiperda, Pseudoplusia includens, Trichoplusia ni*, or *Diatraea grandiosella*.

The present invention is also directed to a kit for detecting *Heliothis virescens* or *Heiicoverpa zea* comprising an antibody. This antibody reacts with a tissue of *Heliothis virescens* and does not detectably react with a tissue of *Heiicoverpa zea*, or the antibody reacts with a tissue of *Heiicoverpa zea* and does not detectably react with a tissue of *Heliothis virescens*. Ideally, the tissue is an egg tissue. The antibody is preferably a monoclonal antibody, and may belong to the immunoglobulin isotype IgG (e.g., IgG1 and IgG2a). Advantageously, if the monoclonal antibody reacts with a tissue of *Heliothis virescens* and does not detectably react with a tissue of *Heiicoverpa zea*, then the monoclonal antibody is produced by the hybridoma cell line Hv-6-12D-1F-4A or Hv-6-12D-6F-4D. If the monoclonal antibody reacts with a tissue of *Heiicoverpa zea* and does not detectably react with a tissue of *Heliothis verescens*, then the monoclonal antibody is produced by the hybridoma cell line Hz4-6G-2E-5B or Hz4-6G-2E-9B. Preferably, thmonoclonal antibody does not detectably react with tissue (e.g., egg tissue) of *Spodoptera exigua, Spodoptera frugiperda, Pseudoplusia includens, Trichoplusia ni*, or *Diatraea grandiosella*.

The present invention is also directed to the hybridoma cell lines Hv-6-12D-1F-4A, Hv-6-12D-6F-4D, Hz4-6G-2E-5B and Hz-4-6G-2E-9B, and is also monoclonal antibodies produced by the hybridoma cell lines Hv-6-12D-6F4D and Hz4-6G-2E-9B.

The following hybridoma cell lines have been deposited with the American Type Culture Collection (ATCC), 10801 University Boulevard, Manassas, Va., 20110–2209, USA:

HZ-4-6G-2E-9B (ATCC designation HB-12527, deposited on May 14, 1998);

Hv-6-12D-6F-4D (ATCC designation HB-12502, deposited on Apr. 8, 1998).

All restrictions on access thereto will be withdrawn upon grant of a U.S. patent on this application.

DETAILED DESCRIPTION OF THE PREFERRED EMBODIMENTS

The present invention is illustrated more specifically by referring to the following Example. However, nothing in this Example shall be taken as a limitation upon the oveiall scope of the invention.

EXAMPLE

Insects.

The following insects were all laboratory-reared using established procedures (King et al 1985 (J. Econ. Entomiol. 78:1166–1172); Davis 1989 (In *Toward Insect Resistant Maize for the Third World: Proceedings of the International Symposium on Methodologies for Developing Host Plant Resistance to Maize Insects*, pp. 27–36, CIMMIT: Mexico, D.F.)): *Spodoptera exigua* (Hubner), beat armyworm, *Spodoptera frugiperda* (Smith), fall armyworm, *Trichoplusia ni* (Hubner), cabbage looper, *Pseudoplusia includens* (Walker), soybean looper, *Diatraea grandiosella* Dyar, southwestern cormborer, *Heliothis virescens* (F.), tobacco budworm, and *Heiicoverpa zea* (3 Boddie), bollworm.

Experimental Animals and Cell Lines.

Pathogen free BALB/c and RBF/DnJ mice were obtained from Charles River and Jackson Laboratories, respectively. The Institutional Animal Care and Use Committee of Mississippi State University monitored the animal care and use procedures. Myeloma cell lines were Ag8.653 and Fox-Ny.

Antibody Production.

The following hybridoma cell lines have been deposited with the American Type Culture Collection (ATCC), 10801 University Boulevard, Manassas, Va., 20110–2209, USA:

HZ-4-6G-2E-9B (ATCC designation HB-12527, deposited on May 14, 1998);

Hv-6-12D-6F-4D (ATCC designation HB-12502, deposited on April 8, 1998).

All restrictions on access thereto will be withdrawn upon grant of a U.S. patent on this application. Antigens (insect egg and larval proteins) were prepared in the manner of Zeng et al 1997 (Arch. Insect Biochem. and Physiol. 34:287–300). Each antigen was obtained by homogenizing separately in a glass-glass homogenizer 1.0 gram each of freshly laid eggs of mated females of *Heliothis virescens* or

*Heiicoverpa zea* in 2 ml phosphate buffered salirne (PBS) containing 2 mM phenyl methyl sulfonyl fluoride (PMSF), 2 mM PTU (phenylthiourea), and 5 mM ethylenediamine-tetraacetic acid-disodium salt (EDTA). The homogenates were centrifuged at 15000 G for 15 min and the internates were used for inmunizing mice. The internates were purified by centrifugal, differential molecular weight filtration using Amicon filters. Further purification was done by mixing the filtered and purified internate and crude homogenate with serum from BALB/c mice or Lewis rats inununized with crude homogenates, refrigerating overnight, centrifuging at 5,000 G for 15 min, and using the supernatant as the purified antigen for the two insect species separately. Thus, mice to be used for obtaining monoclonal antibodies were immunized separately with crude homogenate and purified antigenic proteins from *Heiicoverpa zea* or *Heliothis virescens*. Protein concentrations were determined by the BCA protein assay (Pierce, Rockford, Ill.) with bovine serum albumin (BSA) as the standard. BALB/c or RBF/Dnj mice at 10–14 weeks old were immunized. The first and peritoneal injection at 2–4 week intervals with egg and larval proteins (ca. 38–100 µg per mouse) were in phosphate buffered saline (PBS)/Balanced Salt Solution (BSS) mixed with Freund's adjuvant (1:1), another intraperitoneal injection in BSS/PBS alone was at 24 week intervals. Three days before cell fusion, mice received a final injection intravenously in PBS via a tail vein. Mice were anesthetized with methoxyfluorone and sacrificed on the third day after the final injection. Spleen cells were harvested and fused with Ag8.653 or Fox-Ny myeloma cells using standard procedures (Goding 1980 (J. Immunol. Meth. 39:285–308); Harlow et al 1988 (Antibodies: A laboratory manual, CSH laboratory press: Cold Spring Harbor); Liddell et al 1991 (A practical guide to monoclonal antibodies, pp. 188, John Wiley & Sons Ltd: England) and Taggart et al 1982 (Science 219:1228–1230)). Hybridomas from fusion were placed in adenine aminopterin thymidine (AAT) or hypoxanthine aminopterin thymidine (HAT) medium in 96-well tissue culture plates and kept in a $CO_2$ (about 5%) incubator at 37° C. The cells were checked every day and fed as needed.

Enyzme-Linked bmuunosorbent Assay (ELISA).

Specific antibody-secreting hybridomas were screened by ELISA (Harigai et al 1986 (J. Immunol. Meth. 91:129–138), the contents of which are herein incorporated by reference). First, 100 µl of antigen solution (1 µg/ml) were placed into the wells of an Immulon 1 ELISA plate and incubated at 4° C. overnight; then wells were briefly rinsed once with PBS to remove the unbound antigen from the assay plate and 80 µl of hybridoma supernatant fluid were added to each well. At the same time, immunized mouse serum in blocking buffer (PBS with 0.2% BSA, w/v) was added to some wells as a positive control and to other wells 80 µl of culture medium or normal mouse serum only were added as a negative control. The plate was incubated for one hour at room temperature; the liquid was flicked from the plate and wells were rinsed three times with PBS. The plate was tapped on Kimwipes to remove remaining liquid from the wells. Then 100 µl of anti-mouse Igs peroxidase in blocking buffer (1:1000) were added to each well, and the plate was incubated for one hour; the wells were washed three times with PBS and 200 µl of 2'-Azinobis (3-ethylbenztiazoline-sulfonic acid) (ABTS) substrate solution was added to each well. After color was evident visually, absorbency was measured on a microplate reader (Model 3550-UV, Bio-Rad Laboratories, Hercules, Calif.) at 405 nm.

Hybridoma Cell Cloning and Propagation.

Selected hybridoma cells were cloned at least twice by limiting dilution until all the wells displayed positive antibody production. Origen hybridoma cloning factor (Fisher Scientific Co, Norcross, Ga.) was used during limiting dilution (10–20%, v/v). After limiting dilution, hybridoma cell lines producing species-specific antibody were expanded in tissue culture flasks.

Isotype Determination and Antibody Production.

Monoclonal antibody isotype was determined by using a mouse monoclonal antibody isotyping kit, IsoStrip (Boehringer Mannheim Co., Indianapolis, Ind.). Mass production of monoclonal antibodies was in two ways. One was from cell culture supernates; the other was from ascites production in the peritoneal cavity of the mouse as described by Liddell et al 1991. Isotype was determined for antibody from cell lines Hv-6-12D-6F4D and Hz-4-6G-2E-9B. The monoclonal antibody produced by hybridoma cell line Hv-6-12D-6F-4D was characterized as belonging to the immunoglobulin isotype IgG2a with kappa light chain. The monoclonal antibody produced by hybridoma cell line Hz-4-6G-2E-9B was characterized as belonging to the immunoglobulin isotype IgG1 with kappa light chain.

Species-Specificity of Monoclonal Antibody.

Eggs of seven different lepidopterous species, *Spodoptera exigua, Spodoptera frugiperda, Pseudoplusia includens, Trichoplusia ni, Diatraea grandiosella, Heliothis virescens,* and *Heiicoverpa zea*, were used to test by ELISA species-specific characteristics of antibody from cell lines Hv-6-12D-6F4D and Hz-4-6G-2E-9B. The ELISA procedure was the same as that described above. The monoclonal antibody from hybridoma cell line Hv-6-12D-6F-4D recognized individual eggs of only *Heliothis verescens*, and did not cross-react with individual eggs of *Helicoverpa zea*. The monoclonal antibody from hybridoma cell line Hz-4-6G-2E-9B recognized individual eggs of only *Heiicoverpa zea*, and did not cross-react with individual eggs of *Heliothis virescens*. The monoclonal antibodies from hybridoma cell lines Hv-6-12D-6F-4D and Hz-4-6G-2E-9B did not cross-react with individual eggs of *Spodoptera exigua, Spodoptera frugiperda, Pseudoplusia includens, Trichoplusia ni,* or *Diatraea grandioselia*.

Assay Sensitivity.

ELISA sensitivity to recognize antigen by species-specific antibody was tested by serial dilutions of egg homogenate adjusted to contain protein concentration from 4 ng to 1000 ng. The assays were conducted using antibody secreted by cell lines Hv-6-12D-6F4D and Hz-4-6G-2E-9B at concentrations of 25, 50, and 100 µg/m Reactivity to Developmental Stage.

Reactivity of *Heliothis virescens*-specific monoclonal antibody from Hv-6-12D-6F4D to different *Heliothis virescens* life stages was tested. Individual eggs or small larvae were placed in individual wells of 96-well ELISA plate and squashed in 100 µl of PBS. The hemolymph of large larvae, pupae and adults was collected by the method of Ramaswamy et al 1995 (J. Insect Physiol. 41:501–508). Each of the 50 µl hemolymph samples (5–10 µl per insect) was placed on ice in a small centrifuge tube with 50 µl PBS containing 2 mM phenyl-2-thiourea (PTU), 5 mM ethylene-diaminetetraacetic acid (EDTA), and 1 mM phenyl methyl sulfonyl fluoride (PMSF). The sample was centrifuged at 10,000 g for 10 min at −4° C. to remove hemocytes. Eighty microliters of the supernatant were transferred to a fresh centrifuge tube containing 50 µl of PBS and stored at −80° C. prior to use. Total protein concentration in hemolymph samples was determined by the BCA assay with BSA as the standard. The antigen from different life stages was diluted to 1 µg/ml in PBS before coating ELISA plates. A similar test was conducted also for *Heiicoverpa zea* -specific monoclonal antibody from Hz4-6G-2E-9B.

Specificity Against Field Population.

Eggs from field populations were tested to determine specificity of the monoclonal antibodies. For *Heliothis verescens*, pupae were collected from cotton and pigeon pea fields in Oktibbeha County, Mississippi in Fall 1996. The adults were allowed to emerge at room temperature. After emergence, the species were identified and the moths were fed with 5% sucrose solution (w/v) and held at 26±2° C. in 250-ml plastic cups with moist Kimwipes. The adults were mated and the eggs were collected and used for the assay. For *Helicoverpa zea*, eggs used for the assay were offspring of insectary-reared females and field collected males. All the ELISAs were as described above except individual eggs were squashed in 120 μl PBS. Each egg antigen solution was used to coat two wells (60 μl per well) and, thus, the same individual egg was tested by ELISA using both *Heliothis virescens* and *Heiicoverpa zea* species-specific monoclonal antibodies.

What is claimed is:

1. A method for detecting *Heliothis virescens* comprising the steps of:
   (a) providing a sample suspected of containing a tissue of *Heliothis virescens*;
   (b) contacting the sample with an antibody to form an immunological complex containing the tissue and the antibody; and
   (c) detecting the immunological complex, thereby detecting the tissue,
      wherein the antibody reacts with the tissue of *Heliothis virescens* and does not cross-react with a tissue of *Helicoverpa zea*.

2. The method of claim 1, wherein the method is an enzyme-linked immunosorbent assay.

3. The method of claim 2, wherein the enzyme-linked immunosorbent assay comprises the steps of:
   placing on *Heliothis verenscens* antigen solution into the wells of an ELISA plate and incubating the plate overnight;
   rinsing the wells with phosphate buffered saline (PBS);
   adding supernatant fluid to each well;
   adding *Heliothis verenscens* immunized mouse serum to some wells as a positive control and normal mouse serum to other wells as a negative control;
   incubating said plate for one hour at room temperature;
   rinsing said wells three times with PBS;
   removing remaining liquid from said wells;
   adding anti-mouse Igs peroxidase in blocking buffer to each well;
   incubating said plate for one hour;
   washing said wells three times with PBS;
   adding 3-ethylbenzthiazoline-sulfonic acid substrate solution (2'-Azinobis) to each well;
   measuring absorbency on a microplate reader at 405 nm
   wherein increased absorbance in positive controls indicates the presence of *Heliothis virescens*.

4. The method of claim 1, wherein the tissue is an egg tissue.

5. The method of claim 1, wherein the antibody is a monoclonal antibody.

6. A method for detecting *Heliothis virescens* comprising the steps of:
   (a) providing a sample containing a tissue of *Heliothis virescens*;
   (b) contacting the sample with a monoclonal antibody to form an immunological complex containing the tissue and the antibody, wherein the monoclonal antibody belongs to the immunoglobulin isotype IgG; and
   (c) detecting the immunological complex, thereby detecting the tissue,
      wherein the antibody reacts with the tissue of *Heliothis virescens* and does not cross-react with a tissue of *Helicoverpa zea*.

7. The method of claim 6, wherein the monoclonal antibody belongs to the immunoglobulin isotype IgG1 or IgG2a.

8. A method for detecting *Heliothis virescens* or *Helicoverpa zea* comprising the steps of:
   (a) providing a sample containing a tissue of *Heliothis virescens* or *Helicoverpa zea*;
   (b) contacting the sample with a monoclonal antibody to form an immunological complex containing the tissue and the antibody; and
   (c) detecting the immunological complex, thereby detecting the tissue,
      wherein, if the method is a method for detecting *Heliothis verescens*, then the monoclonal antibody is produced by a hybridoma cell line selected from the group consisting of ATCC NO. HB-12502, and the antibody reacts with the *Heliothis virescens* and does not cross-react with the *Helicoverpa zea*; and
      wherein, if the method is a method for detecting *Helicoverpa zea*, then the monoclonal antibody is produced by a hybridoma cell line selected from the group consisting of ATCC NO. HB-12527, and the antibody reacts with the Helicoverva zea and does not cross-react with the *Heliothis virescens*.

9. The method of claim 5, wherein the monoclonal antibody does not react with a tissue of a species belonging to the group consisting of *Spodoptera exigua, Spodoptera frugiperda, Pseudoplusia includens, Trichoplusia ni*, and *Diatraea grandiosella*.

10. The method of claim 9, wherein the tissue of a species belonging to the group consisting of *Spodoptera exigua, Spodoptera frugiperda, Pseudoplusia includens, Trichoplusia ni*, and *Diatraea grandiosella* is an egg tissue.

11. A kit for detecting *Heliothis virescens* comprising an antibody, wherein the antibody reacts with a tissue of *Heliothis virescens* and does not cross-react with a tissue of *Helicoverpa zea*.

12. The kit of claim 11, wherein the tissue is an egg tissue.

13. The kit of claim 11, wherein the antibody is a monoclonal antibody.

14. A kit for detecting *Heliothis virescens* comprising a monoclonal antibody, wherein the monoclonal antibody belongs to the immunoglobulin isotype IgG, and wherein the monoclonal antibody reacts with a tissue of *Heliothis virescens* and does not cross-react with a tissue of *Helicoverpa zea*.

15. The kit of claim 14, wherein the monoclonal antibody belongs to the immunoglobulin isotype IgG1 or IgG2a.

16. A kit for detecting *Heliothis virescens* or *Helicoverpa zea* comprising a monoclonal antibody
   wherein, if the monoclonal antibody reacts with a tissue of *Heliothis virescens* and does not cross-react with a tissue of *Helicoverpa zea*, then the monoclonal antibody is produced by a hybridoma cell line selected from the group consisting of ATCC NO. HB-12502
   wherein, if the monoclonal antibody reacts with a tissue of *Helicoverpa zea* and does not cross-react with a tissue of *Heliothis verescens*, then the monoclonal antibody is produced by a hybridoma cell line selected from the group consisting of ATCC NO. HB-12527.

17. The kit of claim 13, wherein the monoclonal antibody does not react with tissue of a species belonging to the group consisting of *Spodoptera exigua, Spodoptera frugiperda,*

Pseudoplusia includens, Trichoplusia ni, or *Diatraea grandiosella*.

18. The kit of claim 17, wherein the tissue is an egg tissue.

19. A hybridoma cell line selected from the group consisting of ATCC NO. HB-12502 and ATCC NO. HB-12527.

20. A monoclonal antibody produced by a hybridoma cell line selected from the group consisting of ATCC NO. HB12502 and ATCC NO. HB-12527.

* * * * *

UNITED STATES PATENT AND TRADEMARK OFFICE
CERTIFICATE OF CORRECTION

PATENT NO.   : 6,235,485 B1
DATED        : May 22, 2001
INVENTOR(S)  : Sonny B. Ramaswamy et al.

It is certified that error appears in the above-identified patent and that said Letters Patent is hereby corrected as shown below:

Title page,
Line 3, OTHER PUBLICATIONS: *"Helcoverpa Zea"* should read
-- *Helicoverpa Zea* --.
ABSTRACT
Line 6, "cross-reict" should read -- cross-react --.

Column 1,
Line 26 *"Helicoverpa Zea"* should read -- *Helicoverpa zea* --.
Line 43, *"Heiicoverpa zea"* should read -- *Helicoverpa zea* --.

Column 2,
Line 7, "inmnunoreactivity" should read -- immunoreactivity --.
Line 17, "enzyme4 inked" should read -- enzyme-linked --.
Line 21 and 22, *"Heiicoverpa zea"* should read -- *Helicoverpa zea* --.
Line 24-25, "immunosorbelt" should read -- immunosorbent --.
Line 26, "Stuart etal" should read -- Stuart et al --
Line 31, "inslar *Heiicoverpa* zea should read -- instar *Helicoverpa zea* --.
Lines 39-40, 51, 52-53, 54, 66 *"Heiicoverpa zea"* should read -- *Helicoverpa zea* --.
Line 59, "Goodman etal" should read -- Goodman et al --.
Line 63, "inmuunogen" should read -- immunogen --.
Line 67, "Helicoverpa" should read -- *Helicoverpa* --.

Column 3,
Line 1, "Heliothis" should read -- *Heliothis* --.
Lines 1, 7, 15, 18, 19, 27, 29, 31, 38, 39, 40, 48, 56, 58-59, 60, 66, *"Heiicoverpa zea"* should read -- *Helicoverpa zea* --.
Line 11, "Greenstone etal" should read -- Greenstone et al --.

Column 4,
Line 2, *"Heiicoverpa zea"* should read -- *Helicoverpa zea* --.
Line 5-6, "thmonoclonal" should read -- the monoclonal --.
Line 30, "oveiall" should read -- overall --.
Line 45, "cormborer" should read -- cornbore --.
Line 46, *"Heiicoverpa zea"* should read -- *Helicoverpa zea* --.

UNITED STATES PATENT AND TRADEMARK OFFICE
CERTIFICATE OF CORRECTION

PATENT NO. : 6,235,485 B1
DATED : May 22, 2001
INVENTOR(S) : Sonny B. Ramaswamy et al.

It is certified that error appears in the above-identified patent and that said Letters Patent is hereby corrected as shown below:

Column 5,
Lines 1, 15, "Heiicoverpa zea" should read -- *Helicoverpa zea* --.
Line 1, "salirne" should read -- saline --.
Line 6, "inmunizing" should read -- immunizing --.
Line 10, "inununized" should read -- immunized --.
Line 24, "24 week" should read -- 2-4 week --.

Column 6,
Lines 24, 32, "Heiicoverpa zea" should read -- *Helicoverpa zea* --.
Line 45, "100 μg/m" should read -- 100 μg/ml. --.
Line 55, "50 μI PBS" should read -- 50 μl PBS --.
Line 66, "Heiicoverpa zea -specific" should read -- *Helicoverpa zea*-specific --.

Column 7,
Line 8, "26±2° C." should read -- 26±2°C --.

Line 17, "*Heiicoverpa zea* " should read -- *Helicoverpa zea* --.
Line 37, "on *Heliothis verenscens*" should read -- *Heliothis virescens* --.
Line 42, "*Heliothis verenscens*" should read -- *Heliothis virescens* --.

Column 8,
Line 20, "*Heliothis verenscens*" should read -- *Heliothis virescens* --.
Line 29, "Helicoverva zea" should red -- *Helicoverpa zea* --.

UNITED STATES PATENT AND TRADEMARK OFFICE
CERTIFICATE OF CORRECTION

PATENT NO. : 6,235,485 B1
DATED : May 22, 2001
INVENTOR(S) : Sonny B. Ramaswamy et al.

It is certified that error appears in the above-identified patent and that said Letters Patent is hereby corrected as shown below:

Column 9,
Line 1, "Pseudoplusia includens, Trichoplusia ni" should read -- *Peudoplusia includens, Trichoplusia ni* --.

Signed and Sealed this

Fifth Day of March, 2002

Attest:

JAMES E. ROGAN
*Director of the United States Patent and Trademark Office*

*Attesting Officer*